(12) United States Patent
Yamasaki et al.

(10) Patent No.: US 7,547,675 B2
(45) Date of Patent: Jun. 16, 2009

(54) CHEMICALLY MODIFIED POLYPEPTIDES

(75) Inventors: Motoo Yamasaki, Machida (JP);
Toshiyuki Suzawa, Yamato (JP); Ken Kobayashi, Hofu (JP); Noboru Konishi, Hofu (JP); Shiro Akinaga, Shizuoka (JP); Kumiko Maruyama, Shizuoka (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 90 days.

(21) Appl. No.: 10/365,418

(22) Filed: Feb. 13, 2003

(65) Prior Publication Data

US 2003/0195339 A1    Oct. 16, 2003

Related U.S. Application Data

(62) Division of application No. 09/230,733, filed as application No. PCT/JP98/02504 on Jun. 5, 1998, now Pat. No. 6,583,267.

(30) Foreign Application Priority Data

Jun. 6, 1997  (JP) ............................... P. 9-149342

(51) Int. Cl.
*A68K 38/16* (2006.01)
*C07K 1/107* (2006.01)

(52) U.S. Cl. .............................. 514/12; 514/2; 530/350; 530/345; 424/280.1

(58) Field of Classification Search .................. 514/12; 530/350, 345; 424/280.1
See application file for complete search history.

(56) References Cited

U.S. PATENT DOCUMENTS

| | | | |
|---|---|---|---|
| 4,732,863 A | 3/1988 | Tomasi et al. | |
| 5,081,111 A | 1/1992 | Akimoto et al. | |
| 5,153,265 A | 10/1992 | Shadle et al. | |
| 5,194,592 A | 3/1993 | Yoshida | |
| 5,342,940 A | 8/1994 | Ono et al. | |
| 5,359,030 A | 10/1994 | Ekwuribe | |
| 6,433,135 B1 * | 8/2002 | El-Tayar et al. | ............. 530/313 |
| 6,583,267 B2 | 6/2003 | Yamasaki et al. | |
| 6,884,419 B1 | 4/2005 | Yokoi et al. | |

FOREIGN PATENT DOCUMENTS

| | | |
|---|---|---|
| CN | 1150434 A | 5/1997 |
| EP | 335423 A1 | 10/1989 |
| EP | 400472 A1 | 12/1990 |
| EP | 0 744 409 A1 | 11/1996 |
| JP | 62-501449 A | 6/1987 |
| JP | 1-316400 A | 12/1989 |
| JP | 3-95200 A | 4/1991 |
| JP | 03236400 | 10/1991 |
| JP | 6-319537 | 11/1994 |
| WO | WO 86/04145 A1 | 7/1986 |
| WO | WO 95/23165 A1 | 8/1995 |
| WO | WO 96/11953 | 4/1996 |
| WO | 98/55500 | 12/1998 |

OTHER PUBLICATIONS

Lissoni et al. Database Caplus, DN 129:298630; European Urology (1997), 31(2), 178-181.*
Zink, et al., "Secondary structure of human granulocyte colony-stimulating factor derived from NMR spectroscopy," pp. 435-439, *Elsevier Science Publishers B.V.*
Zalipsky, S. Bioconjugate Chem., 6, 150-165.
Arfin et al, PNAS, vol. 92, pp. 7714-7718, Aug. 1995 "Eukaryotic methionyl aminopeptidases: Two classes of cobalt-dependent enzymes".
Zheng et al, J of Bacteriology, Jun. 2005, p. 3671-3677 "Characterization of Two New Aminopeptidases in *Escherichia coli*".
Bregani ER, et al., Recenti Prog Med. Jun. 1995;86(6):231-3 (Abstract).
Eileen M. Lynch, PhD, LE Magazine Jan. 2004, printed from the web Aug. 11, 2005, http://www.alternativehealth.co.nz/emifs.melatoninmain.htm.
McGraw-Hill Dictionary of Scientific and Technical Terms, Fourth Edition, p. 823 (1989).
Bioconjug. Chem., vol. 4, No. 6, (1993) p. 554-559.

* cited by examiner

*Primary Examiner*—Michael Borin
(74) *Attorney, Agent, or Firm*—Nixon & Vanderhye P.C.

(57) ABSTRACT

The present invention relates to a chemically modified polypeptide in which at least one of hydroxyl groups in the polypeptide molecule is modified with a polyalkylene glycol derivative; a method for producing the modified polypeptide; a method of treatment using the modified polypeptide; use of the modified polypeptide; a pharmaceutical preparation comprising the modified polypeptide; and a composition for treatment comprising the modified polypeptide.

11 Claims, No Drawings

CHEMICALLY MODIFIED POLYPEPTIDES

The present application is a divisional of application Ser. No. 09/230,733, filed Feb. 3, 1999 (now U.S. Pat No. 6,583, 267) which is a 371 U.S. national phase of International Application No. PCT/JP98/02504, filed Jun. 5, 1998, which designated the U.S., and claims benefit of JP9-149342, filed Jun. 6, 1997.

TECHNICAL FIELD

The present invention relates to a chemically modified polypeptide in which at least one of the hydroxyl groups in the polypeptide molecule is modified with a polyalkylene glycol derivative; a method for producing the modified polypeptide; a method of treating a patient having reduced granulocytes or thrombocytes using the modified polypeptide; a composition for the treatment comprising the modified polypeptide; and use of the modified polypeptide.

BACKGROUND ART

A chemically modified polypeptide in which at least one of amino groups, carboxyl groups, mercapto groups or guanidino groups in the polypeptide molecule is modified with a polyalkylene glycol derivative (WO 95/023165) and modification of free thiol groups of cysteine residues in the polypeptide molecule are known (EP 0668353). However, when at least one of such amino groups, carboxyl groups, mercapto groups, guanidino groups or free thiol groups of cysteine residues in the polypeptide molecule is modified with a polyalkylene glycol derivative, the activity of the polypeptide may be markedly or completely lost.

For example, the activity of interleukin-15 completely disappears when its amino group(s) are modified with polyethylene glycol [*J. Biol. Chem.*, 272:2312 (1997)].

Nothing is known about a chemically modified polypeptide in which at least one of the hydroxyl groups in the polypeptide molecule is modified with a polyalkylene glycol derivative.

Great attention has been directed toward the development of (1) a method for the analysis of influences of hydroxyl groups upon the activity of a polypeptide, in a case where the hydroxyl group concerned is in the active site of the polypeptide, (2) a novel chemical modification method which can avoid a probable case where the biological activity of a polypeptide is considerably spoiled when the polypeptide is treated by a conventional chemical modification method, and a chemically modified polypeptide obtained by the method, and (3) a novel method which can improve resistance of polypeptide against protease, freezing-thawing and denaturing agents.

DISCLOSURE OF THE INVENTION

The present invention relates to a chemically modified polypeptide in which at least one of the hydroxyl groups in the polypeptide molecule is modified with a polyalkylene glycol derivative; a method for producing the modifying polypeptide; a method of treating a patient having reduced granulocytes or thrombocytes using the modifying polypeptide; use of the modifying polypeptide; a pharmaceutical preparation comprising the modifying polypeptide; and a composition for the treatment comprising the modifying polypeptide.

With regard to the polypeptide which can be used in the present invention, any polypeptide can be used so long as it contains a hydroxyl group and has a physiological activity or a pharmacological activity. Examples include those having an activity, such as asparaginase, glutaminase, uricase, superoxide dismutase, lactoferin, streptokinase, plasmin, adenosine deaminase, interleukin-1 to 13, interleukin-15, interferon-α, interferon-β, interferon-γ, human granulocyte colony-stimulating factor (hereinafter referred to as "hG-CSF"), and the like.

Examples of a polypeptide having an hG-CSF activity include a polypeptide comprising the amino acid sequence represented by SEQ ID NO:1, a polypeptide comprising a partial amino acid sequence of the sequence, a polypeptide comprising an amino acid sequence in which some parts of amino acids of the sequence are substituted by different amino acids [*Nature*, 319:415 (1986), Japanese Published Unexamined Patent Application No. 267292/88, Japanese Published Unexamined Patent Application No. 299/88, WO 87/01132] and the like. Specific examples of the polypeptide comprising an amino acid sequence in which some parts of amino acids of the amino acid sequence represented by SEQ ID NO:1 are substituted by different amino acids (hG-CSF derivatives) are shown in Table 1.

TABLE 1

| Position from the N-terminal amino acid (hG-CSF of SEQ ID NO:1) | Substituted amino acid in various hG-CSF derivatives | | | | | | | | | | | |
|---|---|---|---|---|---|---|---|---|---|---|---|---|
| | a) | b) | c) | d) | e) | f) | g) | h) | i) | j) | k) | l) |
| 1st (Thr) | * | Val | Cys | Tyr | Arg | * | Asn | Ile | Ser | * | Ala | * |
| 3rd (Leu) | Glu | Ile | Ile | Ile | Thr | Thr | Glu | Thr | Thr | * | Thr | * |
| 4th (Gly) | Lys | Arg | Arg | Arg | Arg | Arg | Arg | Arg | Arg | Arg | Tyr | * |
| 5th (Pro) | Ser | Ser | Ser | Ser | Ser | Ser | Ser | Ser | Ser | * | Arg | * |
| 17th (Cys) | Ser | Ser | Ser | Ser | Ser | Ser | Ser | Ser | Ser | Ser | Ser | Ser |

*: unsubstituted amino acid

Peptide (a) of Table 1 is represented in the Sequence Listing as SEQ ID NO:2.
Peptide (b) of Table 1 is represented in the Sequence Listing as SEQ ID NO:3.
Peptide (c) of Table 1 is represented in the Sequence Listing as SEQ ID NO:4.
Peptide (d) of Table 1 is represented in the Sequence Listing as SEQ ID NO:5.
Peptide (e) of Table 1 is represented in the Sequence Listing as SEQ ID NO:6.

Peptide (f) of Table 1 is represented in the Sequence Listing as SEQ ID NO:7.

Peptide (g) of Table 1 is represented in the Sequence Listing as SEQ ID NO:8.

Peptide (h) of Table 1 is represented in the Sequence Listing as SEQ ID NO:9.

Peptide (i) of Table 1 is represented in the Sequence Listing as SEQ ID NO:10.

Peptide (j) of Table 1 is represented in the Sequence Listing as SEQ ID NO:11.

Peptide (k) of Table 1 is represented in the Sequence Listing as SEQ ID NO:12.

Peptide (l) of Table 1 is represented in the Sequence Listing as SEQ ID NO:13.

Examples of the polyalkylene glycol derivative include polyethylene glycol derivatives, polypropylene glycol derivatives, polyethylene glycol-polypropylene glycol copolymer derivatives, and the like.

The chemically modified polypeptide of the present invention can be produced using a chemical modifying agent comprising the above polyalkylene glycol derivative, and compounds represented by the following formula (I) can be exemplified as preferred chemical modifying agents.

The compounds include polyalkylene glycol derivatives represented by $$R^1\text{-}(M)_n\text{-}X\text{—}R^2 \quad (I)$$

{wherein $R^1$ represents an alkyl group or an alkanoyl group; M represents

or

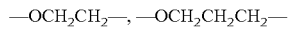

(wherein r and s are the same or different, and each represents an optionally changeable positive integer); n is an optionally changeable positive integer; X represents a bond, O, NH or S; and $R^2$ represents

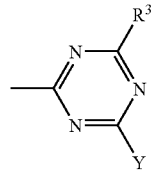

<wherein $R^3$ represents OH, halogen or

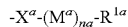

(wherein $X^a$, $M^a$, $R^{1a}$ and na each has the same meanings as the above X, M, $R^1$ and n, respectively) and Y represents halogen or

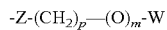

[wherein Z represents O, S or NH; and W represents a carboxyl group or a reactive derivative thereof, or

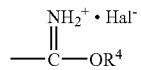

(wherein $R^4$ represents an alkyl group, and Hal represents halogen); p is an integer of 0 to 6; and m is 0 or 1]>,

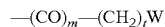

(wherein t is an integer of 0 to 6; and m and W have the same meanings as defined above),

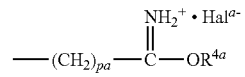

(wherein $Hal^a$, pa and $R^{4a}$ each has the same meanings as the above Hal, p and $R^4$, respectively),

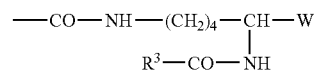

(wherein $R^3$ and W have the same meanings as defined above),

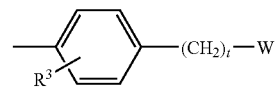

(wherein $R^3$, t and W have the same meanings as defined above),

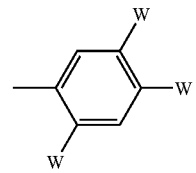

(wherein W has the same meaning as defined above),

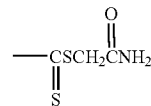

or

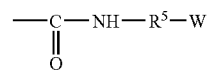

(wherein $R^5$ represents a residue in which an amino group and a carboxyl group are removed from an amino acid; and W has the same meaning as defined above)}.

With regard to the above compound represented by formula (I), examples of the alkyl group represented by $R^1$, $R^4$ or the like include straight or branched alkyl groups having 1 to 18 carbon atoms, such as methyl, ethyl, propyl, isopropyl, butyl, isobutyl, sec-butyl, tert-butyl, pentyl, isopentyl, hexyl, isohexyl, heptyl, octyl, isooctyl, decyl, dodecyl, tetradecyl, hexadecyl, octadecyl, and the like; examples of the alkanoyl group represented by $R^1$ include straight or branched alkanoyl groups having 1 to 18 carbon atoms, such as formyl, acetyl, propionyl, butyryl, valeryl, pivaloyl, pentanoyl, lauroyl, myristoyl, palmitoyl, stearoyl, and the like; examples of the halogen represented by R3, Y, Hal or the like include chlorine, bromine and iodine atoms; examples of the reactive derivative of a carboxyl group represented by W or the like include acid halides, such as an acid chloride, an acid bromide, and the like, active esters, such as a p-nitrophenyl ester, an N-oxysuccinimide ester, and the like, and mixed acid anhydrides with monoethyl carbonate, monoisobutyl carbonate and the like; and examples of the amino acid represented by $R^5$ include glycine, L-alanine, L-valine, L-leucine, L-serine, D-alanine, D-valine, D-leucine, D-serine, β-alanine, and the like. The positive integer represented by n, r or s is 1 to 20,000, preferably 50 to 5,000 for n, and 1 to 5,000 for r and s.

The polyalkylene glycol derivatives have a molecular weight of 500 to 1,000,000, preferably 3,000 to 1,000,000.

A plurality of hydroxyl groups may be present in the polypeptide molecule, and chemical modification of at least one of these groups may be sufficient when the polypeptide is chemically modified.

Examples of the hydroxyl group in the polypeptide molecule include a hydroxyl group of a serine or threonine residue, preferably a hydroxyl group of a serine residue.

The polypeptide can be chemically modified by reacting a chemical modifying agent, such as a polyalkylene glycol derivative selected from a group consisting of polyethylene glycol derivatives, polypropylene glycol derivatives, polyethylene glycol-polypropylene glycol copolymer derivatives and the like, with a polypeptide having a hydroxyl group.

Examples of the method for reacting the hydroxyl group in a polypeptide molecule with a chemical modifying agent such as polyethylene glycol derivatives or polypropylene glycol derivatives include the methods described in Japanese Published Unexamined Patent Application No. 316400/89, Biotech. Lett., 14:559-564 (1992), BIO/TECHNOLOGY, 8:343-346 (1990), and the like, and modified methods thereof. That is, specific examples of the methods which can be used include methods wherein a polyethylene glycol derivative or a polypropylene glycol derivative is added to an aqueous solution of a protein which has been adjusted to a pH of 6 to 10 in an amount of 1 to 200 moles per protein, and is allowed to react at a temperature of 0 to 37° C. for 1 hour to 3 days.

Examples of the method for reacting the hydroxyl group in a polypeptide molecule with a polyethylene glycol-polypropylene glycol copolymer derivative include the methods described in Japanese Published Unexamined Patent Application No. 59629/84, Japanese Published Unexamined Patent Application No. 176586/85, WO 89/06546, EP 0539167A2, and the like, and modified methods thereof. That is, specific examples of the methods which can be used include methods wherein a chemical modifying agent selected from a group consisting of polyethylene glycol-polypropylene glycol copolymer derivatives is added to an aqueous solution of a protein which has been adjusted to a pH of 6 to 10 in an amount of 1 to 200 moles per protein, and is allowed to react at a temperature of 0 to 37° C. for 1 hour to 3 days.

Modification of at least one hydroxyl group in the polypeptide molecule with a polyalkylene glycol derivative by the above method can provide (1) a method for the analysis of influences of the hydroxyl group upon the activity of a polypeptide, in a case where the hydroxyl group concerned is in the active site of the polypeptide, (2) a novel chemical modification method which can avoid diminishing the biological activity of a polypeptide when the polypeptide is treated by a conventional chemical modification method, and a chemically modified polypeptide obtained by the method, and (3) a novel method which can improve a polypeptide's resistance to protease, freezing-thawing or denaturing agents, and a chemically modified polypeptide having improved resistance against protease, freezing-thawing or denaturing agents.

The chemically modified polypeptide of the present invention specifically described is an example in which a polypeptide having an hG-CSF activity is used as a polypeptide.

A chemically modified polypeptide in which at least one hydroxyl group in hG-CSF or a hG-CSF derivative is chemically modified with a chemical modifying agent represented by the following formula (Ia) or (Ib) can be exemplified as the chemically modified polypeptide of the present invention.

Chemical Modifying Agent (Ia):

{wherein $R^1$, n and X have the same meanings as defined above; and $R^{2a}$ represents

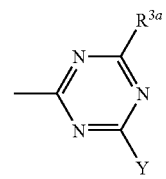

[wherein $R^{3a}$ represents OH, halogen or

(wherein $X^b$, $R^{1b}$ and nb each has the same meanings as the above X, $R^1$ and n, respectively)]}.

Chemical modifying agent (Ib):

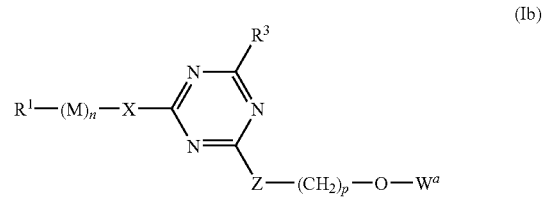

(wherein $R^1$, M, $R^3$, Z, n and p have the same meanings as defined above; and $W^a$ represents a carboxyl group or a reactive derivative thereof).

At least one molecule of polyethylene glycol derivatives, polypropylene glycol derivatives or polyethylene glycol-polypropylene glycol copolymer derivatives is bonded to a chemically modified hG-CSF or a chemically modified hG-CSF derivative. Thus, the chemically modified hG-CSF or the chemically modified hG-CSF derivative can be used as a mixture or by separating a compound to which one or more molecules are attached.

Separation of the chemically modified hG-CSF or the chemically modified hG-CSF derivative can be carried out using various types of chromatography, such as ion exchange chromatography, gel filtration chromatography, reverse phase chromatography, hydrophobic chromatography, and the like, and methods, such as ammonium sulfate fractionation and the like, which are generally used for the separation of long chain polypeptides and the like.

The degree of chemical modification can be confirmed by monitoring changes in the mobility of the chemically modified hG-CSF using a sodium dodecyl sulfate-polyacrylamide gel electrophoresis (SDS-PAGE) method.

The polypeptide content according to the present invention can be measured by the following assay methods.

Assay Method 1:

The polypeptide content is measured by the Lowry method [Lowry O. E. et al., *J. Biol. Chem.*, 193:265 (1951)].

Assay Method 2:

The polypeptide content is calculated by carrying out SDS-PAGE in accordance with the method of Laemmli [U.K. Laemmli, *Nature*, 227:680 (1970)], staining the polypeptide separated on the gel with Coomassie Brilliant Blue and then measuring it by a chromatoscanner (CS-930, Shimadzu Corp.).

The chemically modified polypeptide of the present invention can be used as such or in various dosage formulations.

The pharmaceutical preparations of the present invention can be produced by mixing an effective amount of a chemically modified polypeptide as the active ingredient uniformly with a pharmaceutically acceptable carrier. It is preferred that these pharmaceutical preparations are in a unit dosage form suitable for injection administration.

Injections can be prepared as solutions using a chemically modified polypeptide and a carrier comprising distilled water, a salt solution, a glucose solution or a mixture of a salt solution and a glucose solution. They are also prepared as solutions, suspensions or dispersions in the conventional way using appropriate auxiliaries. They can be also prepared as freeze-dried preparations by freeze-drying the solutions. Although freeze-drying conditions are not particularly limited, a freeze-dried product is generally obtained by freezing at −50° C. or less for 1 to 5 hours, drying at a shelf temperature of −20° C. to 0° C. for 24 to 48 hours under a vacuum degree of 50 to 150 mTorr and then drying at a shelf temperature of 10° C. to 30° C. for 16 to 24 hours under a vacuum degree of 50 to 100 mTorr.

Also, the chemically modified polypeptide preparations can contain various generally used pharmaceutical carriers, fillers, diluents, stabilizers, adsorption preventing agents and the like.

In the case of a chemically modified polypeptide of the present invention, for example a neutrophil and thrombocyte growth enhancing preparation containing a chemically modified hG-CSF or a chemically modified hG-CSF derivative, its dose and its administration schedule are decided depending on its mode of administration, age and body weight of each patient, the disease to be treated and morbid state of each patient; however, a pharmaceutical preparation containing a chemically modified hG-CSF or a chemically modified hG-CSF derivative in an amount of 15 μg to 1.5 mg, preferably 25 to 500 μg, per adult is usually administered 1 to 7 times per week.

Examples of the administration method of the chemically modified polypeptide preparation of the present invention include intravenous injection, subcutaneous injection, and the like, as well as administration as suppositories or nasal drops.

Next, pharmacological activities of the chemically modified polypeptide of the present invention are described by Test Examples.

Test Example 1

Growth Promoting Activity of Chemically Modified hG-CSF and Chemically Modified hG-CSF Derivatives Upon Mouse Leukemia Cell NFS60:

The activity of the G-CSF derivative, chemically modified hG-CSF derivative and chemically modified G-CSF obtained in Reference Example 1 and Examples 5, 14, 17 and 20, which will be described later, to enhance growth of mouse leukemia cell NFS60 [K. Holmes et al., *Proc. Natl. Acad. Sci. USA*, 82:6687 (1985)] was measured in accordance with the method of Asano et al. [Yakuri to Chiryo, 11:2767 (1991)]. Each compound in respective concentrations shown in Tables 2-1 and 2-2 was allowed to act upon the cells, with the results also shown in Tables 2-1 and 2-2.

TABLE 2-1

| Compound | Conc. (ng/ml) | NFS60 cell growth promoting activity (%)[*1] |
|---|---|---|
| hG-CSF derivative of Ref. Ex. 1 | 12.5 | 100 |
| Mono-substituted 1 of Ex. 5 | 12.5 | 100 |
| Mono-substituted 2 of Ex. 5 | 12.5 | 100 |
| Di-substituted of Ex. 5 | 12.5 | 100 |
| Tri-substituted 1 of Ex. 5 | 12.5 | 72 |
| Tri-substituted 2 of Ex. 5 | 12.5 | 93 |
| hG-CSF | 5 | 100 |
| Mono-substituted 1 of Ex.14 | 5 | 86 |
| Mono-substituted 2 of Ex.14 | 5 | 81 |
| Di-substituted of Ex. 14 | 5 | 81 |

[*1]Shown by a relative value (%) based on the activity (=100) of the hG-CSF derivative (12.5 ng/ml) obtained in Reference Example 1 or of hG-CSF (5 ng/ml).

TABLE 2-2

| Compound | Conc. (ng/ml) | NFS60 cell growth promoting activity (%)[*1] |
|---|---|---|
| hG-CSF derivative of Ref. Ex. 1 | 25 | 100 |
| Tri-substituted 1 of Ex. 17 | 25 | 92 |
| Tri-substituted 2 of Ex. 17 | 25 | 80 |
| Di-substituted of Ex. 17 | 25 | 99 |
| Tri-substituted 1 of Ex. 20 | 25 | 65 |
| Tri-substituted 2 of Ex. 20 | 25 | 73 |
| Di-substituted of Ex. 20 | 25 | 98 |

[*1]Shown by a relative value (%) based on the activity (=100) of the hG-CSF derivative (25 ng/ml) obtained in Reference Example 1.

Test Example 2

Effect to Promote Recovery of Thrombopenia in Total Body Radiation Mice:

Four animals per group of male BALB/c mice (6 weeks of age) were radiated to the total bodies (hereinafter referred to as "Rx") with 3 Gy per mouse by a 137 Cs radiation source (RI-433, manufactured by Toshiba) and then reared in a clean rack of a specified pathogen-free (SPF) rearing, environment facility. They were freely provided with drinking water and feed. As a non-treated control group, mice with no radiation were reared in a manner similar thereto.

Each of chemically modified hG-CSF derivatives obtained in Example 4 which will be described later was dissolved in physiological saline, and the chemically modified hG-CSF derivative solution was subcutaneously administered to mice once on the next day of Rx in a dose of 5 µg/0.2 ml per animal.

Blood samples were periodically collected from the murine vein of eyeground to measure the number of platelets by an automatic blood cell counter (CC-180A, manufactured by Toa Iyo Denshi) The results are shown in Table 3.

In the mice treated with total body radiation of 3 Gy, a considerable decrease in the number of platelets was observed, and the number of platelets became the lowest on 8 to 9 days after Rx and then gradually increased but did not recover to the level before the radiation treatment. On the other hand, decrease in the number of platelets was inhibited in the mice to which the chemically modified hG-CSF derivative was administered, and the number of platelets increased markedly on and after the 8th or 9th day and completely recovered on the 11th or 12th day to the same level before the radiation treatment. The similar effect was observed in a group in which the administration was carried out on the next day and 5th day after Rx.

TABLE 3

| Chemically modified hG-CSF derivative | Average number of platelets (%) *1 Days after radiation | | | | | |
|---|---|---|---|---|---|---|
| | 0 | 6 | 8 | 10 | 11 | 12 |
| Not administered | 100 | 58.9 | 26.6 | 35.1 | 38.3 | 45.1 |
| Di-substituted of Ex. 4 | 100 | 55.1 | 30.5 | 62.7 | 98.5 | 103.6 |

*1Shown by a relative value (%) based on the average number of platelets (=100) in the total body radiation-untreated control group.

Test Example 3

Leukocyte Increasing Action in Mice:

Using SPF/VAF mice (BALB/cAnNCrj line, males, 8 weeks of age, 4 animals per group) which were preliminarily reared after purchase from Charles River Japan, leukocyte increasing activity in normal mice was confirmed.

Di-substituted obtained in Example 5 (0.34 mg/ml) was diluted to 100 or 10 µg/ml using physiological saline, and subcutaneously administered once at a rate of 10 µl/g (mouse weight). Thus, the dose was 1 or 0.1 mg/kg. As a control group, physiological saline was subcutaneously administered once. Blood samples were collected before the administration and periodically from the next day after the administration, and the number of peripheral blood cells was measured using an automatic blood cell counter (Sysmex F800).

As the results, the number of leukocytes in both administered groups increased to 2.4 to 2.6 times higher level than that of the control group 2 days after the administration. Thereafter, this drug effect attenuated in the 0.1 mg/kg administration group and returned to a similar level of the control group 4 days after the administration, but the number of leukocytes in the 1 mg/kg administration group continued to increase even after 2 days after administration and reached a level 3.5 times higher than that in the control group 4 days after administration. Thereafter, the number returned to a level similar to the control group on the 7th day after the administration.

Examples and Reference Examples are shown below.

BEST MODE FOR CARRYING OUT THE INVENTION

Example 1

Preparation of Polyethylene Glycol-Modified hG-CSF Derivative Reaction Solution:

The hG-CSF derivative prepared in Reference Example 1 was adjusted to 4.6 mg/ml using a phosphate buffer (pH 7.5), and 12 ml of the thus adjusted solution was mixed with 205.5 mg of N-hydroxysuccinimide ester of monomethoxypolyethylene glycol propionate (M-SPA-20,000, manufactured by Shearwater Polymer) and the mixture was stirred at 4° C. for a whole day and night to prepare a polyethylene glycol-modified hG-CSF derivative reaction solution (1).

Example 2

Preparation of Polyethylene Glycol-Modified hG-CSF Derivative Reaction Solution:

The hG-CSF derivative prepared in Reference Example 1 was adjusted to 4.6 mg/ml using a phosphate buffer (pH 7.5), and 12 ml of the thus adjusted solution was mixed with 469.8 mg of N-hydroxysuccinimide ester of carboxymethyl-monomethoxypolyethylene glycol (M-SCM-20,000, manufactured by Shearwater Polymer) and the mixture was stirred at 4° C. for a whole day and night to prepare a polyethylene glycol-modified hG-CSF derivative reaction solution (2).

Example 3

Preparation of Polyethylene Glycol-Modified hG-CSF Derivative Reaction Solution:

The hG-CSF derivative prepared in Reference Example 1 was adjusted to 4.6 mg/ml using a phosphate buffer (pH 7.5), and 6.6 ml of the thus adjusted solution was mixed with 96.9 mg of N-hydroxysuccinimide ester of monomethoxypolyethylene glycol propionate (M-SSPA-20,000, manufactured by Shearwater Polymer) and the mixture was stirred at 4° C. for a whole day and night to prepare a polyethylene glycol-modified hG-CSF derivative reaction solution (3).

Example 4

Isolation of Polyethylene Glycol-Modified Component:

The polyethylene glycol-modified hG-CSF derivative reaction solution (2) prepared in Example 2 (protein content, 55 mg) was diluted 5 times with a 20 mM acetate buffer (pH 4.5) containing 150 mM of sodium chloride and passed through a column packed with Sephacryl S-400 (manufactured by Pharmacia) which had been equilibrated in advance with the same buffer, and the eluates were fractionated. By this operation, a fraction mainly containing a component modified with two molecules of polyethylene glycol (Di-substituted) and a crude fraction mainly containing a component modified with one molecule of polyethylene glycol (Mono-substituted) were obtained.

Each of these fractions was passed through a column packed with TSK gel G4000SW$_{XL}$ (7.8 mm I.D.×300 mm, manufactured by Tosoh Corp.) to obtain a fraction containing Di-substituted or Mono-substituted. Thereafter, each of these fractions was purified using SP-5PW (21.5 mm I.D.×150 mm, manufactured by Tosoh Corp.) under the following conditions to obtain one species of the main component of Di-substituted (0.39 mg/ml×3.0 ml) and one species of the main component of Mono-substituted (0.55 mg/ml×3.0 ml).

SP-5PW purification conditions:
Column: SP-5PW (21.5 mm I.D.×150 mm) (manufactured by Tosoh Corp.)
Detection: 280 nm
Solution A: 20 mM acetate buffer (pH 4.5)
Solution B: 20 mM acetate buffer (pH 4.5) containing 0.5 M sodium chloride
Elution: linear density gradient elution from solution A to solution B Example 5

Isolation of Polyethylene Glycol-Modified Component:

The polyethylene glycol-modified hG-CSF derivative reaction solution (1) prepared in Example 1 (protein content, 55 mg) was diluted 5 times with a 20 mM acetate buffer (pH 4.5) containing 150 mM of sodium chloride and passed through a column packed with Sephacryl S-400 (manufactured by Pharmacia) which had been equilibrated in advance with the same buffer, and the eluates were fractionated. By this operation, a crude fraction containing a component modified with three molecules of polyethylene glycol (Tri-substituted), a crude fraction containing a component modified with two molecules of polyethylene glycol (Di-substituted) and a crude fraction containing a component modified with one molecules of polyethylene glycol (Mono-substituted) were obtained.

Each of these fractions was passed through a column packed with TSK gel G4000SW$_{XL}$ (7.8 mm I.D.×300 mm, manufactured by Tosoh Corp.) to obtain a fraction containing Tri-substituted, Di-substituted or Mono-substituted. Thereafter, each of these fractions was purified using a cation exchange column, SP-5PW (manufactured by Tosoh Corp.), under the same conditions described in Example 4 to obtain two species of the main component of Tri-substituted (Tri-substituted 1: 1.4 mg/ml×0.5 ml, Tri-substituted 2: 1.0 mg/ml×0.8 ml), one species of the main component of Di-substituted (0.34 mg/ml×3.0 ml) and two species of the main components of Mono-substituted (Mono-substituted 1: 0.48 mg/ml×0.4 ml, Mono-substituted 2: 1.58 mg/ml×0.5 ml).

As will be described in later examples, the hydroxyl group of the 66 position Ser counting from the N-terminus of Mono-substituted 1 and the N-terminal Met of Mono-substituted 2 were modified with one molecule of polyethylene glycol.

Example 6

Isolation of Polyethylene Glycol-Modified Component:

The polyethylene glycol-modified hG-CSF derivative reaction solution (3) prepared in Example 3 (protein content, 30 mg) was diluted 5 times with a 20 mM acetate buffer (pH 4.5) containing 150 mM of sodium chloride and passed through a column packed with Sephacryl S-400 (manufactured by Pharmacia) which had been equilibrated in advance with the same buffer, and the eluates were fractionated. By this operation, a crude fraction containing a component modified with two molecules of polyethylene glycol (Di-substituted) was obtained.

This fraction was passed through a column packed with TSK gel G4000SW$_{XL}$ (7.8 mm I.D.×300 mm, manufactured by Tosoh Corp.) to obtain a fraction containing Di-substituted.

The thus obtained fraction was purified using a cation exchange column, SP-5PW (manufactured by Tosoh Corp.) under the same conditions described in Example 4 to obtain one species of the main component of Di-substituted (0.43 mg/ml×3.0 ml).

Example 7

Peptide Mapping of hG-CSF Derivative:

The hG-CSF derivative prepared in Reference Example 1 was adjusted to 2 mg/ml using a phosphate buffer (pH 7.5), a 1.0 ml portion of the thus adjusted solution was treated with V8 protease (manufactured by Seikagaku Kogyo) under the conditions described in "High Performance Liquid Chromatography of Protein and Peptide (II), Kagaku Zokan 117 (153-160 (1990); published by Kagaku Dojin)" and then a 50 μl portion of the thus treated solution was injected into an HPLC to carry out HPLC analysis under the following conditions.

Conditions for HPLC analysis:
Column: PROTEIN & PEPTIDE C18 (4.6 mm I.D.×250 mm, VYDAC)
Solution A: 0.1% trifluoroacetic acid
Solution B: 90% acetonitrile containing 0.1% trifluoroacetic acid
Elution: linear density gradient elution from solution A to solution B
Detection: 215 nm
Flow rate: 0.5 ml/min Nine peaks were found on the analytical pattern of the hG-CSF derivative digested with VB protease. When each of the peaks was separated and its molecular weight analysis was carried out, these peaks were assigned as shown in Table 4.

TABLE 4

Peptide mapping of hG-CSF derivative by V8 protease

| Peak No. | Peptide fragment | Molecular weight analyzed (calculated) * (Na addition) |
|---|---|---|
| 1 | 94–98 | 524.5* (502) |
| 2 | 20–33 | 1512.8 (1514) |
| 3 | 34–46 | 1648.8 (1649) |
| 4 | 163–174 | 1438.9 (1440) |
| 5 | −1–19 | 2241.7 (2241) |
| 6 | 124–162 | 4028.0 (4029) |
| 7 | 105–123 | 2263.8* (2240) |
| 8 | 47–93 | 5060.5 (5060) |
| 9 | 99–123 | 2836.9 (2836) |

Example 8

Estimation of Polyethylene Glycol Binding Position by Peptide Mapping:

Each of Mono-substituted 1, Mono-substituted 2, Di-substituted, Tri-substituted 1 and Tri-substituted 2 obtained in Example 5 was digested with a protease by a procedure similar to the hG-CSF derivative peptide mapping described in Example 7.

As the results, disappearance or considerable reduction of specified peaks was found in Mono-substituted 1, Di-substituted, Tri-substituted 1 and Tri-substituted 2 obtained in Example 5 (Table 5).

TABLE 5

Peptide mapping of purified polyethylene glycol-modified hG-CSF derivative component (comparison with unmodified hG-CSF derivative)

| Component | Disappeared or markedly reduced peak No. |
|---|---|
| Mono-substituted 1 of Ex. 5 | 8 |
| Mono-substituted 2 of Ex. 5 | 5 |
| Di-substituted of Ex. 5 | 5, 8 |
| Tri-substituted 1 of Ex. 5 | 3, 5, 8 |
| Tri-substituted 2 of Ex. 5 | 3, 5, 8 |

It is believed that the HPLC peaks of the polyethylene glycol-linked peptide fragments will change when compared with the analytical pattern of the hG-CSF derivative of Example 7. Based on the results of Table 4, it was estimated that the binding position of polyethylene glycol was at least a peptide residue (including an N-terminal amino group) corresponding to a fragment of −1 to 19 amino acid residues (peak 5) of the hG-CSF derivative in the case of Mono-substituted 2, Di-substituted, Tri-substituted 1 and Tri-substituted 2 shown in Example 5.

With regard to Mono-substituted 2, it was found that the N-terminal Met residue of Mono-substituted 2 was modified with one molecule of polyethylene glycol, because its N-terminal sequence was not observed when the sequence was measured using a protein sequencer PPSQ-10 manufactured by Shimadzu Corp.

With regard to Tri-substituted 1 and Tri-substituted 2, it was estimated that polyethylene glycol was also bound to at least a peptide residue (including an amino group of Lys) corresponding to a fragment of 34 to 46 amino acid residues (peak 3) of the hG-CSF derivative.

In addition, since the peak 8 disappeared or markedly reduced in each of Mono-substituted 1, Di-substituted, Tri-substituted 1 and Tri-substituted 2, it was estimated that polyethylene glycol was also bound to a peptide residue (excluding free amino groups of lysine and the like) corresponding to a fragment of 47 to 93 amino acid residues of each of these components.

Example 9

Estimation of Polyethylene Glycol Binding Position by Peptide Mapping:

The fraction of Di-substituted obtained in Example 6 was digested with a protease by a procedure similar to the hG-CSF derivative peptide mapping described in Example 7.

When compared with the analytical pattern of the hG-CSF derivative of Example 7, disappearance or considerable reduction of the specified peaks shown in Table 6 was found in Di-substituted obtained in Example 6.

TABLE 6

Peptide mapping of purified polyethylene glycol-modified hG-CSF derivative component (comparison with unmodified hG-CSF derivative)

| Component | Disappeared or markedly reduced peak No. |
|---|---|
| Di-substituted of Ex. 5 | 5, 8 |

It is predicted that the HPLC peaks of the polyethylene glycol-linked peptide fragments will change when compared with the analytical pattern of the hG-CSF derivative of Example 7. Based on the results of Table 5, similar to the case of Example 8, it was estimated that binding positions of polyethylene glycol were a peptide residue (including an N-terminal amino group) corresponding to a fragment of −1 to 19 amino acid residues and a peptide residue (excluding free amino groups of lysine and the like) corresponding to a fragment of 47 to 93 amino acid residues of the hG-CSF derivative in the case of Di-substituted shown in Example 6.

Example 10

Estimation of Polyethylene Glycol Binding Position by Peptide Mapping:

The binding position of polyethylene glycol on Di-substituted obtained by a procedure similar to that of Example 4 was examined by peptide mapping in a manner similar to those in Examples 7 and 8. It was estimated that polyethylene glycol was also bound to a peptide residue (including an N-terminal amino group) corresponding to a fragment of −1 to 19 amino acid residues and a peptide residue (excluding free amino groups of lysine and the like) corresponding to a fragment of 47 to 93 amino acid residues of the hG-CSF derivative in the case of Di-substituted shown in Example 4.

Example 11

Purification of Polyethylene Glycol-Modified Peptide:

A fragment of polyethylene glycol-bound peptide was isolated from Di-substituted component by the following procedure in order to examine polyethylene glycol binding amino acid residues in the peptide fragment corresponding to the 47 to 93 position amino acid residues containing no free amino groups, of the hG-CSF derivative or hG-CSF, which was the polyethylene glycol binding position confirmed in Di-substituted of Examples 4, 5 and 6, Tri-substituted 1 and Tri-substituted 2 of Example 5, Mono-substituted 1 of Example 5, Mono-substituted 1 and Di-substituted of Example 14, Di-substituted, Tri-substituted 1 and Tri-substituted 2 of Example 17 or Di-substituted, Tri-substituted 1 and Tri-substituted 2 of Example 20.

That is, 30 ml of a fraction containing Di-substituted as the main component (protein concentration, 2.2 mg/ml) was obtained by a cation exchange chromatography column, SP-5PW, in a manner similar to that in Example 5 from a polyethylene glycol-modified hG-CSF derivative reaction solution prepared in a manner similar to that in Example 1. Next, this was digested with thermolysin (manufactured by Sigma). Using a gel filtration column (Sephacryl S-300, manufactured by Pharmacia), the enzyme reaction solution was fractionated to obtain the desired polyethylene glycol-bound peptide fraction (about 30 mg).

The result of mass spectrometry (MALDI-TOF MS) of the peptide fraction was 22155.89 (M+H), and the result of amino acid analysis showed Ser 2.7 (3), Pro 1.0 (1), Leu 1.0 (1) and Cys 0.9 (1).

Based on the results of mass spectrometry and amino acid analysis, it was estimated that the sample isolated by the above procedure was a fragment in which polyethylene glycol was bound to a peptide of position 61 residue to the 66 position residue [LeuSerSerCysProSer (leucyl-seryl-seryl-S-amidomethylcysteinyl-prolyl-serine) residue] of the hG-CSF derivative.

Example 12

Determination of Polyethylene Glycol Binding Position by $^1$H-NMR:

A peptide, LeuSerSerCysProSer (leucyl-seryl-seryl-cysteinyl-prolyl-serine) corresponding to the 61 to 66 position amino acid residues of the hG-CSF derivative was synthesized by a peptide solid phase synthesis method (PSSM 8, Shimadzu Corp.) and amidomethylated under the conditions shown in "High Performance Liquid Chromatography of Protein and Peptide (II), Kagaku Zokan 117 (153-160 (1990); published by Kagaku Dojin)" and then the thus amidomethylated peptide (leucyl-seryl-seryl-S-amidomethylcysteinyl-prolyl-serine) was purified by reverse phase HPLC. A 0.6 mg portion of the amidomethylated peptide was dissolved in deuterium-substituted dimethyl sulfoxide ($d_6$-DMSO) to carry out $^1$H-NMR analysis (500 MHz). In a similar manner, $^1$H-NMR analysis was carried out using 20 mg of the polyethylene glycol-bound peptide obtained in Example 11. Chemical shift of protons (other than those originating from polyethylene glycol) observed by each analysis is shown in Tables 7 and 8. From the results, all of the protons originating from the γOH groups of three Ser residues were confirmed in the amidomethylated peptide obtained by synthesis. On the other hand, some phenomena were observed in the polyethylene glycol-bound peptide obtained in Example 11, in addition to the signal of protons originating from polyethylene glycol, that the proton originating from γOH group of the 66 position Ser residue of the hG-CSF derivative was not observed, that β proton of the same Ser residue was shifted to about 0.6 ppm-lower magnetic field and that amido proton of the same Ser residue gave a broad signal in comparison with other amido protons. On the basis of the above results, it was confirmed that the binding position of polyethylene glycol was the 66 position Ser residue of the hG-CSF derivative.

TABLE 7

Chemical shift (ppm) of protons in NMR analysis of amidomethylated peptide synthesized

| Residue | NH | CαH | CβH | Others |
|---|---|---|---|---|
| Leu 61 | 8.06 | 3.86 | 1.52, 1.57 | γH1.67, δCH₃0.92 |
| Ser 62 | 8.66 | 4.47 | 3.57, 3.64 | γOH5.13 |
|  | *8.66* | *4.49* | *3.63* | *γOH5.04* |
| Ser 63 | 8.03 | 4.32 | 3.58 | γOH4.85 |
|  | *8.06* | *4.32* | *3.57* | *γOH4.80* |
| Cys 64 | 8.19 | 4.68 | 2.63, 2.96 | CH₂3.12, NH₂7.05, 7.42 |
|  | *7.97* | *4.60* | *2.63, 2.90* | *CH₂3.12, NH₂7.10, 7.45* |
| Pro 65 |  | 4.42 | 1.91, 2.02 | γH1.86, δH3.61 |
|  |  | *4.80* | *1.98, 2.20* | *γH1.83, δH3.45, 3.40* |
| Ser 66 | 7.98 | 4.23 | 3.60, 3.70 | γOH4.94 |
|  | *8.40* | *4.24* | *3.80, 3.72* | *γOH4.90* |

The italic type represents Cis-Pro.

TABLE 8

Chemical shift (ppm, excluding the polyethylene glycol moiety) of protons in NMR analysis of polyethylene glycol-modified peptide isolated from polyethylene glycol-modified hG-CSF derivative

| Residue | NH | CαH | CβH | Others |
|---|---|---|---|---|
| Leu 61 |  | 3.66 | 1.44, 1.56 | γH1.70, δCH₃0.90 |
|  |  | *3.73* | *1.47, 1.60* | *γH1.67, δCH₃0.90* |
| Ser 62 | 8.51 | 4.43 | 3.57, 3.64 | γOH5.17 |
|  | *8.90* | *4.37* | *3.64* |  |
| Ser 63 | 8.03 | 4.30 | 3.60 | γOH4.85 |
|  | *8.06* | *4.21* | *3.58, 3.63* |  |
| Cys 64 | 8.18 | 4.68 | 2.68, 3.03 | CH₂3.12, NH₂7.02, 7.43 |
|  | *8.08* | *4.62* | *2.67, 2.90* | *CH₂3.12, NH₂7.02, 7.62* |
| Pro 65 |  | 4.33 | 1.87, 2.02 | γH1.86, δH3.67 |
|  |  | *4.60* | *2.12, 2.04* | *γH1.72, 1.83, δH3.40, 3.52* |
| Ser 66 | 7.88 | 4.28 | 4.17, 4.32 |  |
|  | *7.66* | *4.21* | *4.16, 4.46* |  |

The italic type represents Cis-Pro.

Example 13

Preparation of Polyethylene Glycol-Modified hG-CSF Reaction Solution:

A 4.0 ml portion of a 4.0 mg/ml solution of hG-CSF prepared using a phosphate buffer (pH 7.5) was mixed with 83 mg of N-hydroxysuccinimide ester of monomethoxypolyethylene glycol propionate (M-SPA-20,000, manufactured by Shearwater Polymer) and the mixture was stirred at 4° C. for a whole day and night.

Example 14

Isolation of Polyethylene Glycol-Modified Component:

The polyethylene glycol-modified reaction solution prepared in Example 13 (protein content, 16 mg) was diluted 5 times with a 20 mM acetate buffer (pH 4.5) containing 150 mM of sodium chloride and fractionated using a column packed with Sephacryl S-400 (manufactured by Pharmacia) which had been equilibrated in advance with the same buffer. By this operation, a fraction mainly containing a component modified with two molecules of polyethylene glycol (Di-substituted) and a crude fraction mainly containing a component modified with one molecules of polyethylene glycol (Mono-substituted) were obtained. Each of these fractions was applied to a column packed with TSK gel G4000SW$_{XL}$ (7.8 mm I.D.×300 mm, manufactured by Tosoh Corp.) to obtain a fraction containing Di-substituted or Mono-substituted. Thereafter, each of these fractions was purified using SP-5PW (21.5 mm I.D.×150 mm, manufactured by Tosoh Corp.) to obtain one species of the main component of Di-substituted (0.61 mg/ml×0.6 ml) and two species of the main component of Mono-substituted (Mono-substituted 1: 0.46 mg/ml×1.0 ml, Mono-substituted 2: 0.61 mg/ml×0.7 ml).

Example 15

Estimation of Polyethylene Glycol Binding Position by Peptide Mapping:

Each of Mono-substituted 1, Mono-substituted 2 and Di-substituted obtained in Example 14 was digested with a protease by a procedure similar to the hG-CSF derivative peptide mapping described in Example 7.

As the results, disappearance or considerable reduction of specified peaks was found when compared with the analytical pattern of hG-CSF as was found in Example 8.

According to a method similar to that in Example 8, the binding position of polyethylene glycol was estimated as follows. Mono-substituted 1:

The position was within a peptide fragment (not including free amino groups of lysine and the like) corresponding to the 47 to 93 position residues of the amino acid sequence represented by SEQ ID NO:1, and it was confirmed according to the method described in Example 12 that the hydroxyl group of the 66 position Ser counting from the N-terminus was modified with one molecule of polyethylene glycol.

Mono-Substituted 2:

The position was within a peptide fragment (including an N-terminal amino group) corresponding to the −1 to 19 position residues of the amino acid sequence represented by SEQ ID NO:1, and it was confirmed according to the method described in Example 7 that the N-terminal Met was modified with one molecule of polyethylene glycol.

Di-Substituted:

A peptide fragment (including an N-terminal amino group) corresponding to the −1 to 19 position residues, and a peptide fragment (not including free amino groups of lysine and the like residues) corresponding to the 47 to 93 position residues, of the amino acid sequence represented by SEQ ID NO:1.

Example 16

Preparation of Polyethylene Glycol-Modified hG-CSF Derivative Reaction Solution:

The hG-CSF derivative prepared in Reference Example 1 was adjusted to 0.9 mg/ml using a phosphate buffer (pH 7.2) to obtain 600 ml of the adjusted solution. While cooling in an ice bath, the thus obtained solution was mixed with 8.7 g of N-hydroxysuccinimide ester of 2,4-bis(o-methoxy-polyethylene glycol)-6-(3-carboxypropylamino)-s-triazine obtained by a method similar to that in Reference Example 2, and the mixture was stirred at 4° C. for 48 hours to prepare a polyethylene glycol-modified hG-CSF derivative reaction solution (4).

Example 17

Isolation of Polyethylene Glycol-Modified Component:

The polyethylene glycol-modified hG-CSF derivative reaction solution (4) prepared by a method similar to that in Example 16 (protein content, 40 mg) was passed through a column packed with Sephacryl S-300 (manufactured by Pharmacia) which had been equilibrated in advance with a 20 mM acetate buffer (pH 4.5) containing 150 mM of sodium chloride, and the eluates were fractionated. By this operation, a crude fraction containing a component modified with three molecules of polyethylene glycol (Tri-substituted) and a crude fraction containing a component modified with two molecules of polyethylene glycol (Di-substituted) were obtained.

Each of these fractions was purified using a cation exchange column SP-5PW (manufactured by Tosoh Corp.) in a manner similar to that in Example 4 to obtain two species of the main components of Tri-substituted (Tri-substituted 1: 0.49 mg/ml×1.3 ml, Tri-substituted 2: 0.57 mg/ml×1.5 ml) and one species of the main component of Di-substituted (1.94 mg/ml×1.2 ml).

Example 18

Estimation of Polyethylene Glycol Binding Position by Peptide Mapping:

Polyethylene glycol-binding positions of Di-substituted, Tri-substituted 1 and Tri-substituted 2 obtained in Example 17 were examined by a procedure similar to the peptide mapping described in Examples 7 and 8.

Also in Di-substituted, Tri-substituted 1 and Tri-substituted 2 obtained in Example 17, it was estimated that polyethylene glycol was bound to a peptide fragment (including an N-terminal amino group) corresponding to the −1 to 19 position residues of the hG-CSF derivative and to a peptide fragment (not including free amino groups of lysine and the like) corresponding to the 47 to 93 position residues of the hG-CSF derivative. In Tri-substituted 1 and Tri-substituted 2, it was estimated that polyethylene glycol was also bound to at least a peptide fragment (including an amino group of Lys) corresponding to the 34 to 46 position residues (peak 3) of the hG-CSF derivative.

Example 19

Preparation of Polyethylene Glycol-Modified hG-CSF Derivative Reaction Solution:

The hG-CSF derivative prepared in Reference Example 1 was adjusted to 0.9 mg/ml using a phosphate buffer (pH 7.3) to obtain 560 ml of the adjusted solution. While cooling in an ice bath, the thus obtained solution was mixed with 22.4 g of N-hydroxysuccinimide ester of 2,4-bis(o-methoxypolyethylene glycol)-6-(3-carboxypropyl-amino)-s-triazine obtained by a method described similar to that in Reference Example 4, and the mixture was stirred at 4° C. for 48 hours to prepare a polyethylene glycol-modified, hG-CSF derivative reaction solution (5).

Example 20

Isolation of Polyethylene Glycol-Modified Component:

The polyethylene glycol-modified hG-CSF derivative reaction solution (5) prepared by a method similar to that in Example 19 (protein content, 15 mg) was passed through a column packed with Sephacryl S-400 (manufactured by Pharmacia) which had been equilibrated in advance with a 20 mM acetate buffer (pH 4.5) containing 150 mM of sodium chloride, and the eluates were fractionated. By this operation, a crude fraction containing a component modified with three molecules of polyethylene glycol (Tri-substituted) and a crude fraction containing a component modified with two molecules of polyethylene glycol (Di-substituted) were obtained.

Each of these fractions was purified using a cation exchange column SP-5PW (manufactured by Tosoh Corp.) in a manner similar to that in Example 4 to obtain two species of the main components of Tri-substituted (Tri-substituted 1: 3.53 mg/ml×0.4 ml, Tri-substituted 2: 0.26 mg/ml×2.1 ml) and one species of the main component of Di-substituted (0.84 mg/ml×1.2 ml).

Example 21

Estimation of Polyethylene Glycol Binding Position by Peptide Mapping:

Polyethylene glycol-binding positions of Di-substituted, Tri-substituted 1 and Tri-substituted 2 obtained in Example 20 were examined by a procedure similar to the peptide mapping described in Examples 7 and 8. Also in Di-substituted, Tri-substituted 1 and Tri-substituted 2 obtained in Example 20, it was estimated that polyethylene glycol was bound to a peptide fragment (including an N-terminal amino group) corresponding to the −1 to 19 position residues of the hG-CSF derivative and to a peptide fragment (not including free amino groups of lysine and the like) corresponding to the 47 to 93 position residues of the hG-CSF derivative. In Tri-substituted 1 and Tri-substituted 2, it was estimated that polyethylene glycol was also bound to at least a peptide fragment (including an amino group of Lys) corresponding to the 34 to 46 position residues of the hG-CSF derivative.

Example 22

Protease Resistance of Chemically Modified Polypeptide:

A 0.5 ml portion of each of the two species of Mono-substituted components obtained in Example 14 was passed through a gel filtration column [Sephadex G-25 (NAP-5, manufactured by Amersham-Pharmacia)] which had been equilibrated with a 10 mM phosphate buffer (pH 5.0), and the eluates were recovered in 1.0 ml portions.

Each of the thus recovered fractions was diluted with a 10 mM phosphate buffer (pH 5.0) to adjust the protein concentration to 0.2 mg/ml.

A 2 ml portion of each of the thus diluted fractions was mixed with 0.2 mg/ml of thermolysin (enzyme/substrate ratio=1/50) and the mixture was allowed to react at 30° C.

Samples were periodically collected from the reaction solutions in 100 µl portions and mixed with 2 µl of acetic acid to terminate the reaction.

Using 50 µl of each of the reaction-terminated samples, HPLC analysis was carried out under the following conditions.

HPLC Analysis Conditions:

Column: TSK gel G4000SW$_{XL}$ (7.8 mm I.D.×300 mm) (manufactured by Tosoh)

Detection: 280 nm

Mobile phase: 150 mM NaCl/20 mM sodium acetate buffer (pH 4.5)

Flow rate: 0.8 ml/min

Mono-substituted's 1 and 2 were eluted at a retention time of 12 minutes. When these Mono-substituted's were hydrolyzed by thermolysin, the detection peak found at the position of 12 minutes decreases so that the degree of hydrolysis of these Mono substituted's by thermolysin could be confirmed.

Table 9 shows periodic changes in the residual ratio of Mono-substituted's calculated from the decreasing ratio of the detection peak found at the position of 12 minutes.

TABLE 9

Stability against thermolysin

| Reaction time (hr) | Mono-substituted 1 of Ex. 14 | Mono-substituted 2 of Ex. 14 |
|---|---|---|
| 0 | 100 | 100 |
| 15 | 95 | 72 |
| 23 | 89 | 68 |

It was found from the results shown in Table 9 that Mono-substituted 1 in which Ser was modified with polyethylene glycol was more resistant to thermolysin than Mono-substituted 2 in which the N-terminus was modified.

Example 23

Stability of Chemically Modified Polypeptide Against Freezing-Thawing:

A 1 ml portion of each of the two species of Mono-substituted components obtained in Example 5 was passed through two gel filtration columns [Sephadex G-25 (NAP-10, manufactured by Amersham-Pharmacia)] which had been equilibrated with a 5 mM sodium acetate buffer (pH 4.5) or a 5 mM sodium acetate buffer (pH 5.0), and the eluates from each column were recovered in 1.5 ml portions.

The protein concentration of each of the thus recovered fractions was adjusted to 300 µg/ml.

Each of the thus adjusted fractions was dispensed in 500 µl portions, frozen at −30° C. and then melted in a water bath at room temperature.

This freezing-thawing treatment was repeated four times, and then the remaining amount (recovery yield) of each modified polypeptide was measured under the gel filtration HPLC conditions described in Example 22.

The results are shown in Table 10.

TABLE 10

| Polyethylene glycol-modified product | Recovery yield (%) after four freezing-melting treatments | |
|---|---|---|
| | pH 4.5 | pH 5.0 |
| Mono-substituted 1 of Ex. 5 | 100 | 101 |
| Mono-substituted 2 of Ex. 5 | 91.3 | 85.5 |

It was found from the results shown in Table 10 that Mono-substituted 1 in which Ser was modified with polyethylene glycol was more stable against freezing-thawing than Mono-substituted 2 in which the N-terminus was modified.

Example 24

In vitro Activity of Chemically Modified Polypeptide:

The activity of the two species of Mono-substituted components obtained in Example 14 to enhance growth of mouse leukemia cell NFS60 [K. Holmes et al., *Proc. Natl. Acad. Sci. USA*, 82:6687 (1985)] was measured in accordance with the method of Asano et al. [Yakuri to Chiryo, 19:2767 (1991)] by the following serial dilution method.

A suspension of the cells washed with G-CSF (−) medium was dispensed in 50 µl portions into wells of a 96 well plate.

Mono-substituted 1 obtained in Example 14 was adjusted to 25 ng/ml, and a 50 µl portion of the adjusted solution was added to the first well and thoroughly mixed to adjust the solution to 12.5 ng/ml.

A 50 µl portion of the solution was removed from the well and added to the second well and thoroughly mixed to adjust the solution to 6.25 ng/ml. By repeating this procedure, 11 steps of two-fold dilution series were prepared.

In the same manner, two-fold dilution series were prepared using Mono-substituted 2 (25 ng/ml) obtained in Example 14 and a standard solution (5 ng/ml) containing the hG-CSF derivative of Reference Example 1. By this method, dilution series of Mono-substituted 2 from 12.5 ng/ml and dilution series of the standard solution from 2.5 ng/ml were prepared in 50 µl portions in respective wells.

The growth activity of NFS60 cells was measured three times for each of the sample solutions and the standard solutions, and relative activity of each Mono-substituted was calculated based on the activity (=100) of the standard solution.

Mono-substituted 1 showed 1.06 to 1.13 times higher activity than Mono-substituted 2.

Reference Example 1

In accordance with the method described in Reference Example 3 of Japanese Examined Patent Application No. 096558/95, a hG-CSF derivative (compound k in Table 1) was obtained from hG-CSF having the amino acid sequence shown in SEQ ID NO:1 by replacing the 1 position threonine with alanine, the 3 position leucine with threonine, the 4 position glycine with tyrosine, the 5 position proline with arginine and the 17 position cystine with serine.

That is, a strain of *Escherichia coli*, W3110 strA (*Escherichia coli* ECfBD28, FERM BP-1479), which has a plasmid pCfBD28 containing a DNA fragment coding for the above-described hG-CSF derivative was cultured at 37° C. for 18 hours in LG medium [prepared by dissolving 10 g of Bacto Tryptone, 5 g of Yeast Extract, 5 g of sodium chloride and 1 g of glucose in 1 liter of water and adjusting its pH to 7.9 with NaOH], a 5 ml portion of the cultured broth was inoculated into 100 ml of MCG medium (0.6% $Na_2HPO_4$ 0.3% $KH_2PO_4$, 0.5% sodium chloride, 0.5% casamino acid, 1 MM $MgSO_4$ and 4 μg/ml of vitamin B1, pH 7.2) containing 25 μg/ml of tryptophan and 50 μg/ml of ampicillin and the mixture was cultured at 30° C. for 4 to 8 hours. Then, 10 μg/ml of a tryptophan inducer 3β-indoleacrylic acid (hereinafter referred to as "IAA") was added to the medium and the culturing was continued for additional 2 to 12 hours. The resulting culture broth was centrifuged at 8,000 rpm for 10 minutes, and the thus collected cells were washed with 30 mM sodium chloride and a 30 mM Tris-HCl buffer (pH 7.5) The thus washed cells were suspended in 30 ml of the above-described buffer and disrupted ultrasonically at 0° C. for 10 minutes using a sonicator (SINIFIER CELL DISRUPTOR 200, OUTPUT CONTROL 2, manufactured by BRANSON SONIC POWER COMPANY). The cell suspension after the ultrasonic disruption was centrifuged at 9,000 rpm for 30 minutes to obtain the cell residue.

Thereafter, the hG-CSF derivative was extracted and purified from the cell residue and solubilized and regenerated, in accordance with the method of Marston et al. [F. A. O. Marston et al., *BIO/TECHNOLOGY*, 2:800 (1984)].

Reference Example 2

Production of N-hydroxysuccinimide Ester of 2,4-bis(o-methoxypolyethylene glycol)-6-(3-carboxy-propylamino)-s-triazine:

412 mg (4.0 mmol) of γ-aminobutyric acid was dissolved in 300 ml of a 0.1 M borate buffer (pH 10), and the resulting solution which was cooled in an ice bath was mixed with 20 g (2 mmol) of 2,4-bis(o-methoxypolyethylene glycol)-6-chloro-s-triazine (manufactured by Seikagaku Kogyo) and the mixture was allowed to react at 4° C. for a whole day and night and then at room temperature for 6 hours.

The reaction solution was adjusted to pH 1 by adding 1 N hydrochloric acid, and then 2,4-bis(o-methoxypolyethylene glycol)-6-(3-carboxypropyl-amino)-s-triazine was extracted with chloroform. The chloroform phase was dried over anhydrous sodium sulfate, the insoluble matters were removed by filtration, and then the solvent was evaporated under reduced pressure to obtain the carboxylic acid derivative.

The carboxylic acid derivative was recrystallized from dry acetone to obtain 15.8 g (1.6 mmol) of crystals of the carboxylic acid derivative.

A 10 g (1.0 mmol) portion of the crystals and 230 mg of N-hydroxysuccinimide were dissolved in 100 ml of anhydrous methylene chloride and, while cooling in an ice bath and in a stream of argon, the resulting solution was mixed with 413 mg of N,N'-dicyclohexylcarbodiimide (DCC) and the mixture was stirred for 30 minutes. After completion of the stirring, the temperature of the reaction mixture was returned to room temperature, and stirred for additional 1.5 hours, the insoluble matters (N,N'-dicyclohexylurea (DCU)) were removed by filtration and then the resulting filtrate was concentrated to 40 ml under reduced pressure.

The concentrate was added dropwise to 600 ml of anhydrous diethyl ether to form a precipitate. The precipitate was washed with anhydrous diethyl ether and then the solvent was removed under reduced pressure to obtain 7.7 g (0.77 mmol) of N-hydroxysuccinimide ester of 2,4-bis(o-methoxy-polyethylene glycol)-6-(3-carboxypropylamino)-s-triazine (yield, 77%).

Reference Example 3

Production of 2,4-bis(o-methoxypolyethylene glycol)-6-(3-carboxypropylamino)-s-triazine:

100 g (8.33 mmol) of thoroughly dried monomethoxypolyethylene glycol having an average molecular weight of 12,000 (manufactured by Nippon Oil & Fats), 9.3 g of zinc oxide (Wako Pure Chemical Industries) and 83.5 g of molecular sieves (Type 4A) (Wako Pure Chemical Industries) were dissolved in dry benzene, and the solution was allowed to stand at room temperature for a whole day and night in a stream of argon.

After removing the molecular sieves, the reaction solution was distilled at 80° C. in a stream of argon using a distillation apparatus and then azeotropically distilled for a whole day and night at 80° C. in a stream of argon using a Soxhlet extractor (for solid phase use) which had been packed with about 100 g of molecular sieves (Type 4A).

The reaction solution obtained by the dehydration reflux was cooled, mixed with 736 mg (4.0 mmol) of cyanuric chloride and then azeotropically distilled for 5 days in a manner similar to that described above. Thereafter, this solution was cooled to room temperature, mixed with 300 ml of dry benzene and then the mixture was centrifuged at 3,600 rpm for 10 minutes to remove insoluble matter.

The thus obtained supernatant was concentrated to 300 ml under reduced pressure and added dropwise to 3,000 ml of dry diethyl ether to form a precipitate. The precipitate was recovered and washed with dry diethyl ether, and then the solvent was removed under reduced pressure to obtain a dry precipitate.

While cooling in an ice bath, 100 g of the dry precipitate was added to a solution prepared by dissolving 1.24 g (12.0 mmol) of γ-aminobutyric acid in 1,000 ml of a 0.1 M borate buffer (pH 10), and the mixture was stirred at 4° C. for a whole day and night. After additional 6 hours of stirring at room temperature, this solution was adjusted to pH 1.0 with 1 N hydrochloric acid and then 2,4-bis(o-methoxypolyethylene glycol)-6-(3-carboxypropyl-amino)-s-triazine was extracted with chloroform.

The chloroform phase containing the compound was dried over anhydrous sodium sulfate and filtered, and then the solvent was removed from the resulting filtrate under reduced pressure. The thus formed white solid was recrystallized from dry acetone to obtain about 90 g of 2,4-bis(o-methoxy-polyethylene glycol)-6-(3-carboxypropylamino)-s-triazine (yield, 90%).

Reference Example 4

Production of N-hydroxysuccinimide Ester of 2,4-bis(o-methoxypolyethylene glycol)-6-(3-carboxy-propylamino)-s-triazine:

25 g (1.0 mmol) of 2,4-bis(o-methoxy-polyethylene glycol)-6-(3-carboxypropylamino)-s-triazine which had been synthesized in a manner similar to that in Reference Example 3 and thoroughly dried and 240 mg of N-hydroxysuccinimide were dissolved in 400 ml of anhydrous methylene chloride and, while cooling in an ice bath and in a stream of argon, the resulting solution was mixed with 431 mg of N,N'-dicyclohexylcarbodiimide (DCC) and the mixture was stirred for 30 minutes.

After completion of the stirring, the reaction mixture was returned to room temperature and stirred for additional 1.5 hours, the insoluble matters (N,N'-dicyclohexylurea (DCU)) were removed by filtration and then the resulting filtrate was concentrated to 160 ml under reduced pressure.

The concentrate was added dropwise to 2,400 ml of anhydrous diethyl ether to form a precipitate, the precipitate was washed with anhydrous diethyl ether and then the solvent was removed under reduced pressure to obtain 21.4 g (0.89 mmol) of N-hydroxysuccinimide ester of 2,4-bis(o-methoxypolyethylene glycol)-6-(3-carboxy-propylamino)-s-triazine (yield, 89%).

INDUSTRIAL APPLICABILITY

The present invention provides a chemically modified polypeptide in which at least one of the hydroxyl groups in the polypeptide molecule is modified with a polyalkylene glycol derivative; a method for producing the modified polypeptide; a method for treatment using the modified polypeptide; use of the modified polypeptide; a pharmaceutical preparation comprising the modified polypeptide; and a composition for treatment comprising the modified polypeptide.

The invention claimed is:

1. A method of treating a patient having reduced granulocytes or thrombocytes, which comprises administering to said patient an effective amount of a chemically modified polypeptide having a granulocyte colony-stimulating factor activity in which the hydroxyl group of at least one serine residue is modified with a polyalkylene glycol derivative, said polypeptide comprising a sequence selected from the group consisting of SEQ ID NOs: 1-13, said method resulting in an increase in the number of granulocytes or thrombocytes in said patient.

2. The method according to claim 1, wherein the polyalkylene glycol derivative has a molecular weight of 500 to 1,000,000.

3. The method according to claim 1, wherein the polypeptide is modified with a chemical modifying agent comprising a polyalkylene glycol derivative.

4. The method according to claim 3, wherein the chemical modifying agent is a polyalkylene glycol derivative represented by the following formula (I):

$$R^1\text{-}(M)_n\text{-}X\text{—}R^2 \quad (I)$$

wherein $R^1$ represents an alkyl group or an alkanoyl group; M represents

—OCH$_2$CH$_2$—, —OCH$_2$CH$_2$CH$_2$— or

—(OCH$_2$CH$_2$)$_r$—(OCH$_2$CH$_2$CH$_2$)$_s$ wherein r and s are the same or different, and each represents an optionally changeable positive integer; n is an optionally changeable positive integer; X represents a bond, O, NH or S; and $R^2$ represents

[triazine structure with $R^3$ and Y substituents]

wherein $R^3$ represents OH, halogen or

—$X^a$-($M^a$)$_{na}$—$R^{1a}$ wherein $X^a$, $M^a$, $R^{1a}$ and na each have the same meanings as the above X, M, $R^1$ and n, respectively; and Y represents halogen or -Z-(CH$_2$)$_p$—(O)$_m$W wherein Z represents O, S or NH; and W represents a carboxyl group or a reactive derivative thereof, or $$\begin{array}{c}\text{NH}_2^+\cdot\text{Hal}^-\\\|\\\text{—C—OR}^4\end{array}$$

wherein $R^4$ represents an alkyl group, and Hal represents halogen; p is an integer of 0 to 6; and m is 0 or 1, —(CO)$_m$—(CH$_2$)$_t$-W wherein t is an integer of 0 to 6, $$\begin{array}{c}\text{NH}_2^+\cdot\text{Hal}^{a-}\\\|\\\text{—(CH}_2)_{pa}\text{—C—OR}^{4a}\end{array}$$

wherein Hal$^a$, pa and $R^{4a}$ each has the same meanings as the above Hal, p and $R^4$, respectively, —CO—NH—(CH$_2$)$_4$—CH—W
                              |
                    $R^3$—CO—NH

[phenyl structure with $R^3$ and (CH$_2$)$_t$—W substituents]

[phenyl structure with three W substituents]

$$\begin{array}{c}\text{O}\\\|\\\text{—CSCH}_2\text{CNH}_2\\\|\\\text{S}\end{array} \quad \text{or} \quad \begin{array}{c}\text{—C—NH—}R^5\text{—W}\\\|\\\text{O}\end{array}$$

wherein $R^5$ represents a residue in which an amino group and a carboxyl group are removed from an amino acid.

5. The method according to claim 3, wherein the chemical modifying agent is a polyalkylene glycol derivative represented by the following formula (Ib):

$$R^1\text{—(M)}_n\text{—X—}[\text{triazine with } R^3]\text{—Z—(CH}_2)_p\text{—O—W}^a \quad (Ib)$$

wherein $W^a$ represents a carboxyl group or a reactive derivative thereof.

6. The method according to claim 1, wherein the chemically modified polypeptide having a granulocyte colony-stimulating factor activity in which the hydroxyl group of at least one serine residue is modified with a polyalkylene glycol derivative, said polypeptide comprising a sequence selected from the group consisting of SEQ ID NOs: 1-13, wherein said sequence selected from the group consisting of SEQ ID NOs: 1-13 has been chemically modified at serine position 66 from the N-terminus with a polyalkylene glycol derivative.

7. The method according to claim 6, wherein the polyalkylene glycol derivative has a molecular weight of 500 to 1,000,000.

8. The method according to claim 6, wherein the polypeptide is modified with a chemical modifying agent comprising a polyalkylene glycol derivative.

9. The method according to claim 8, wherein the chemical modifying agent is a polyalkylene glycol derivative represented by the following formula (I):

$$R^1-(M)_n-X-R^2 \qquad (I)$$

wherein $R^1$ represents an alkyl group or an alkanoyl group; M represents

—OCH$_2$CH$_2$—, —OCH$_2$CH$_2$CH$_2$— or

—(OCH$_2$CH$_2$)$_r$—(OCH$_2$CH$_2$CH$_2$)$_s$— wherein r and s are the same or different, and each represents an optionally changeable positive integer; n is an optionally changeable positive integer; X represents a bond, O, NH or S; and $R^2$ represents

[triazine structure with $R^3$ and Y substituents]

wherein $R^3$ represents OH, halogen or

—X$^a$-(M$^a$)$_{na}$-R$^{1a}$ wherein X$^a$, M$^a$, R$^{1a}$ and na each have the same meanings as the above X, M, $R^1$ and n, respectively; and Y represents halogen or -Z-(CH$_2$)$_p$—(O)$_m$—W wherein Z represents O, S or NH; and W represents a carboxyl group or a reactive derivative thereof, or

[structure: —C(=NH$_2^+$·Hal$^-$)—OR$^4$]

wherein $R^4$ represents an alkyl group, and Hal represents halogen; p is an integer of 0 to 6; and m is 0 or 1, —(CO)$_m$—(CH$_2$)$_t$—W wherein t is an integer of 0 to 6,

[structure: —(CH$_2$)$_{pa}$—C(=NH$_2^+$·Hal$^{a-}$)—OR$^{4a}$]

wherein Hal$^a$, pa and $R^{4a}$ each has the same meanings as the above Hal, p and $R^4$, respectively,

—CO—NH—(CH$_2$)$_4$—CH(—CO—NH—R$^3$)—W

[para-substituted benzene with $R^3$ and (CH$_2$)$_t$—W]

[trisubstituted benzene with three W groups]

[structure: —C(=S)SCH$_2$C(=O)NH$_2$]  or  —C(=O)—NH—R$^5$—W wherein $R^5$ represents a residue in which an amino group and a carboxyl group are removed from an amino acid.

10. The method according to claim 8, wherein the chemical modifying agent is a polyalkylene glycol derivative represented by the following formula (Ib):

$$R^1-(M)_n-X-\text{[triazine with }R^3\text{]}-Z-(CH_2)_p-O-W^a \qquad (Ib)$$

wherein $W^a$ represents a carboxyl group or a reactive derivative thereof.

11. The method according to any one of claims 1, 2-5, 6, and 7-10, wherein the patient having reduced granulocytes or thrombocytes is a patient of granulocytopenia or thrombocytopenia.

* * * * *

SEQUENCE LISTING

```
<160> NUMBER OF SEQ ID NOS: 1

<210> SEQ ID NO 1
<211> LENGTH: 175
<212> TYPE: PRT
<213> ORGANISM: Unknown
<220> FEATURE:
<223> OTHER INFORMATION: Description of Unknown Organism: polypeptide
      having hG-CSF activity

<400> SEQUENCE: 1

Met Thr Pro Leu Gly Pro Ala Ser Ser Leu Pro Gln Ser Phe Leu Leu
 -1   1           5                  10                  15

Lys Cys Leu Glu Gln Val Arg Lys Ile Gln Gly Asp Gly Ala Ala Leu
             20                  25                  30

Gln Glu Lys Leu Cys Ala Thr Tyr Lys Leu Cys His Pro Glu Glu Leu
         35                  40                  45

Val Leu Leu Gly His Ser Leu Gly Ile Pro Trp Ala Pro Leu Ser Ser
     50                  55                  60

Cys Pro Ser Gln Ala Leu Gln Leu Ala Gly Cys Leu Ser Gln Leu His
 65                  70                  75

Ser Gly Leu Phe Leu Tyr Gln Gly Leu Leu Gln Ala Leu Glu Gly Ile
 80                  85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
    145                 150                 155

Phe Leu Glu Val Ser Tyr Arg Val Leu Arg His Leu Ala Gln Pro
160                 165                 170
```